United States Patent

Borzatta

[11] 4,246,201
[45] Jan. 20, 1981

[54] SUBSTITUTED N-(3-PHENYLTHIOPROPYL)-3,3-DIPHENYL-PROPYLAMINES POSSESSING PHARMACOLOGICAL ACTIVITY

[75] Inventor: Valerio Borzatta, Bologna, Italy

[73] Assignee: Alfa Farmaceutici, S.p.A., Bologna, Italy

[21] Appl. No.: 47,226

[22] Filed: Jun. 11, 1979

[51] Int. Cl.³ .................... A01N 33/02; A01N 43/08; C07C 87/28; C07C 143/00
[52] U.S. Cl. ......................... 564/317; 260/326.14 T; 260/343.7; 260/501.18; 260/501.19; 424/262; 424/280; 424/316; 424/330
[58] Field of Search ........... 260/570 R, 501.18, 501.19

[56] References Cited

U.S. PATENT DOCUMENTS 3,884,939  5/1975  Bianchini et al. ................ 260/570 X

OTHER PUBLICATIONS

Burger, "Medicinal Chemistry", Third Ed., Part II, pp. 1562–1569, (1970).

*Primary Examiner*—Robert V. Hines
*Attorney, Agent, or Firm*—Stevens, Davis, Miller & Mosher

[57] ABSTRACT

Compound of formula:

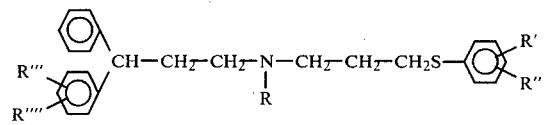

wherein R represents hydrogen or an alkyl group having from 1 to 4 carbon atoms; R', R'', R''' and R'''', equal or different from each other represent hydrogen atoms or OH groups, with the limitation that when R', R'', R''' and R'''' are all hydrogen atoms R cannot be an hydrogen atom and their salts with organic and inorganic pharmaceutically acceptable salts.

The process for the preparation of the compounds of the above general formula are disclosed.

The compounds show a good pharmacological activity and can be used as antiulcer, antispastic spasmolytic drugs.

The compounds can be administered as different pharmaceutical preparations containing an effective dose of the compound in combination or in admixture with excipients suitable for oral or parenteral administration or for topical use.

1 Claim, No Drawings

SUBSTITUTED N-(3-PHENYLTHIOPROPYL)-3,3-DIPHENYL-PROPYLAMINES POSSESSING PHARMACOLOGICAL ACTIVITY

This is a continuation of application Ser. No. 923,586 filed July 11, 1978 and now abandoned.

DETAILED DESCRIPTION OF THE INVENTION

The present invention relates to new products having pharmacological activity as antiulcer antispastic and spasmolitic agents.

It is known from U.S. Pat. No. 3,884,939, in the name of the same Applicant that N-(3'-phenylthiopropyl)-3,3-diphenylpropylamine and its pharmaceutically acceptable salts possess a good antiulcer activity.

It is an object of the present invention to provide new pharmaceutically effective compounds corresponding to the general formula:

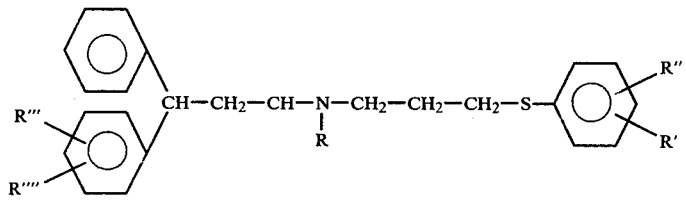

wherein R represents hydrogen, or an alkyl group having from 1 to 4 carbon atoms; R', R", R''' and R'''', equal or different from each other represent hydrogen atoms, or OH groups, with the limitation that when R', R", R''' and R'''' are all hydrogen atoms, R cannot be an hydrogen atom, theirs salts with organic and inorganic pharmaceutically acceptable acid.

The products according to the present invention may be obtained according to one or more of the following processes:

(a) reaction between a primary amine and an haloderivative. An example of such a process is the reaction of 3,3-diphenylpropylamine or its derivative hydroxy-substituted in the phenyl ring with a 3-phenylthio-1-halopropane or its hydroxy-substituted in the phenyl. Another example is the reaction of a 3-phenylthiopropylamine or its hydroxy-substituted in the phenyl with a 3,3-diphenyl-1-halopropane or its hydroxy-substituted in the phenyl;

(b) hydrogenation of a Schiff's base obtained via condensation of a primary amine with an aldehyde;

(c) reaction of a secondary amine with an haloderivative. An example is the reaction between N-(3'-phenylthiopropyl)-3-p-hydroxyphenyl-3-phenyl-propylamine and methyl iodide;

(d) reaction of a 3,3-diphenyl-3'halo-dipropylamine with a thiophenol or with an active derivative thereof;

(e) dealkylation of an alkyloxy-derivative. An example of such a process is the demethylation of N-(3'-phenylthiopropyl)-3-p-methoxyphenyl-3-phenyl-propylamine;

(f) hydrogenation of an amide obtained via condensation of an acyl halide with a primary amine. The hydrogenation is carried out with a complex hydride of aluminum or boron such as for instance lithium-aluminum hydride.

With the expression "salts of pharmaceutically acceptable acids" its is meant to define the salts of the products according to the invention with a nontoxic anion.

Examples of such salts are: hydrochlorides, bromides sulfate, phosphates, nitrates, acetates, propionates, succinates, adipates, glycolates, lactates, malates, ascorbates, piruvates, tartrates, maleates, citrates bicarbonates, palmoates, phenylacetates, benzoates salicylates, alkylsulfates, arylsulfates, glucuronates, salts with methionine, tryptophan, lysine and arginine.

The preferred salts are the hydrochlorides.

The products according to the present invention have shown a good pharmacological activity which makes them suitable to be used as antiulcer, antispastic and/or spasmolytic drugs.

N-(3'-p-hydroxyphenylthiopropyl)-3,3-diphenyl-propylamine, particularly as hydrochloride possesses a strong antiulcer activity combined with a low toxicity.

This product has shown, against ulcers induced in rats by phenylbutazone, inhibition values of 50% and 80% respectively at dosages of 10 and 50 mg/kg given i.p. whereas the apparent $LD_{50}$ is $>1000$ and 150 mg/Kg per o.s. and i.p. respectively.

The pharmaceutically active compounds according to the present invention are useful in the preparation of pharmaceutical preparations containing an effective dose of such products in combination or in admixture with excipients suitable for oral or parenteral administration or for topical use.

Tablets and capsules are preferred. They may contain: (a) diluents e.g. lactose, dextrose, sucrose, mannitol, sorbitol, cellulose and/or glycerol; (b) lubricants e.g. silica, talcum, stearic acid, its magnesium or calcium salts and/or polyethylenglycols, and for the tablets (c) binding agents e.g. aluminum and magnesium silicates, starch, gelatine, tragacanth, methylcellulose, sodium carboxymethylcellulose and/or polyvinylpyrrolidone and occasionally (d) disgregating agents e.g. starch, agar, alginic acid or its sodium salts, enzymes effective on the binding agents and/or (e) absorbents, dyes, flavours and sweeteners.

Injectable composition are preferably aqueous or isotonic solutions or suspensions.

Suppositories and ointments are preferably emulsions or suspensions in fatty or oily substances.

The pharmaceutical compositions may be sterilized and/or may contain adjuvant such as preservatives stabilizers, wetting agents or emulsifiers, solution promoters, salts to regulate the tossicity and/or buffers. The above pharmaceutical preparations may contain, additionally, other substances having pharmacological activity.

The above pharmaceutical preparations are prepared according to conventional methods.

The following examples are supplied with the purpose of illustrating the present invention without limiting in any way the scope thereof.

The thin layer chromatographies (TLC) have been carried out on silica-gel plates Merk $GF_{254}$; as eluent a mixture of isoamyl acetate 60, methanol 20, water 6 and formic acid 5 (parts by volume) has been used.

EXAMPLE 1

Preparation of N-(3-p-hydroxyphenylthiopropyl)-3,3-diphenyl-propylamine hydrochloride 3.8 g (0.012 moles) of 3,3-diphenyl-3'-hydroxydipropylamine hydrochloride (obtained by treatment of the free base in ethanol with gaseous hydrogen chloride, followed by crystallization of the obtained oil first from ethyl acetate and then from n-butanol) in 40 ml anhydrous benzene are added with 0.37 ml (0.004 moles) of $PBr_3$. After 1 hour at room temperature the mixture is refluxed for 1 hour, cooled and poured into a cold solution of sodium bicarbonate at 10%.

The benzene layer is washed twice with water, dried and evaporated. The raw 3,3-diphenyl-3'-bromodipropylamine is obtained as an oil (3.2 g Rf=0.9) and can be used directly for the subsequent reaction. 2.49 g (0.019 moles) of 4-mercaptophenol dissolved in 20 ml methanol are added, under stirring at 40° C., with a solution of 0.22 g (0.0096 moles) of sodium in 8 ml of methanol. The mixture is refluxed, a solution of 6.4 g (0.019 moles) of 3,3-diphenyl-3'-bromodipropylamine in 10 ml methanol is added and again refluxed for 24 hours. After cooling the solvent is evaporated under vacuum. The residue dissolved in chloroform and washed twice hydrochloric acid 6 N. Chloroform is evaporated under vacuum and the residue is crystallized at first from ethylacetate and then from a mixture n-butanol/ethyl ether. Obtained 3.64 g—m.p.=146°–148° C. Rf=0.35.

EXAMPLE 2

Preparation of N-(3'-p-hydroxyphenylthiopropyl)-3,3-diphenyl-propylamine hydrochloride To 6.3 g (0.05 moles) of 4-mercaptophenol in 20 ml methanol is added under stirring at 40° C. a solution of 1.15 (0.05 moles) of sodium in 20 ml methanol. The solution is stirred for 90 minutes at 40°–50° C. To 6.45 g (0.05 moles) of 3-chloropropylamine hydrochloride in 20 ml methanol, is added at cool and under stirring, a solution of 1.15 g (0.05 moles) of sodium in 20 ml methanol.

After stirring off the formed sodium chloride the solution of the sodium salt of 4-mercaptophenol previously prepared is gradually added. After 150 minutes at 60° C. the solid is filtered off, the solution is evaporated, and the residue dissolved in a mixture 1:1 (v/v) of methylene chloride and water.

The solid, consisting of raw 3-p-hydroxyphenylthiopropylamine, is filtered, dissolved in ethanol saturated with hydrogen chloride and added with ethylacetate to precipitate the hydrochloride.

4.6 g of product with m.p. 174°–175° C. are obtained.

To a solution of 4.38 g (0.02 moles) of 3-p-hydroxyphenylthiopropylamine hydrochloride in 30 ml anhydrous ethanol is added a solution of 0.46 g (0.02 moles) of sodium in 10 ml anhydrous ethanol. After stirring at cool for 30 minutes the mixture is brought to reflux. 2.75 g (0.01 moles) of 3,3-diphenylpropylbromide in 20 ml anhydrous ethanol are gradually added and the mixture is refluxed for 24 hours. After cooling the solvent is evaporated under vacuum.

The residue is dissolved in chloroform and the solution is washed twice with sodium hydroxide 10% and twice with hydrochloric acid 6 N.

The organic layer is separated, the solvent evaporated and the residual is dissolved in ethylacetate and recrystallized from a mixture of n-butanol/ethyl ether. Obtained 2.0 g—m.p. 146°–149° C.

EXAMPLE 3

Preparation of N-(3'-phenylthiopropyl)-3-p-hydroxyphenyl-3-phenyl-propylamine hydrochloride To 9.4 g (0.039 moles) of 3-p-methoxyphenyl-3-phenylpropylamine in 60 ml toluene are added 11.5 ml (0.078 moles) of triethylamine and brought to reflux. A solution of 9.0 g (0.039 moles) of 3-phenylthiopropylbromide in 20 ml toluene is gradually added. The mixture is refluxed for 15 hours and after cooling, the hydrobromide of triethylamine is filtered off. The solution is washed three times with water, dried over anhydrous sodium sulfate and evaporated. The obtained oil, is dissolved in 50 ml chloroform and the solution is saturated with hydrogen chloride, washed four times with warm water dried over anhydrous sodium sulfate and the solvent evaporated under vacuum. The product is crystallized from a mixture 1/1 of ethylacetate/ethyl ether.

6.8 g N-(3-phenylthiopropyl-3-p-methoxyphenyl-3-phenylpropylamine hydrochloride having m.p. 138°–140° C. are obtained—Rf=0.4.

To a solution of 0.856 g (0.05 moles) of the above product in 20 ml methylene chloride cooled down to −70° C. is gradually added, while stirring, a precooled solution of 2.5 g (0.01 moles) of boron tribromide in 8 ml of methylene chloride. The temperature is let to increase to the room value and the mixture is stirred for 24 hours. After cooling with brine 22 ml water are added, then 70 ml ethyl ether are added and the pH is brought to neutrality. Ethyl ether is evaporated, chloroform is added and the solution is treated with hydrogen chloride.

The product is filtered off and crystallized from ethylacetate. Obtained 0.5 g; m.p. 113°–115° C. Rf=0.35.

EXAMPLE 4

Preparation of N-(methyl)-N-(3'-phenylthiopropyl)-3-p-hydroxyphenyl-3-phenylpropylamine To a solution of 0.8 g (0.0021 moles) of N-(3-phenylthiopropyl)-3-p-hydroxyphenyl-3-phenylpropylamine in 20 ml methanol and containing 0.3 ml triethylamine are added gradually 0.13 ml (0.0021 moles) methyl iodide.

After 36 hours at room temperature the solvent is evaporated under vacuum and the residue is dissolved in 20 ml benzene. The solution is washed three times with water, dried and evaporated. The residual oil is purified by preparative TLC on a silica-gel plate Merck $GF_{254}$ using as a diluent the mixture benzene 126, ethyl ether 60, acetic acid 18, methanol 1, 0.15 g of oil are obtained. Rf=3.

EXAMPLE 5

Preparation of
N-(methyl)-N-(3'-p-hydroxyphenylthiopropyl)-3,3-diphenylpropylamine To a solution of 0.8 g (0.0021 moles) of N-(3'-p-hydroxyphenylthiopropyl)-3,3-diphenylpropylamine in 20 ml methanol containing 0.3 ml triethylamine are gradually added 0.13 ml (0.0021 moles) methyl iodide. After 36 hours at room temperature the solvent is evaporated under vacuum and the residue is dissolved in 20 ml benzene. The solution is washed three times with water, dried and evaporated.

The obtained oil is purified by preparative TLC using the method disclosed in the preceding example, 0.125 g of oil are obtained. Rf=0.3.

The oil is dissolved in ethanol saturated with hydrogen chloride and the solution evaporated under vacuum. The residue crystallized from ethylacetate obtaining 0.120 g of a product having m.p. 118°–120° C.

EXAMPLE 6

Preparation of N-(methyl)-N-(3'-phenylthiopropyl)-3,3 diphenylpropylamine hydrochloride.

To an aqueous solution of methylamine at 35% is added, gradually and under stirring a solution of 2.5 g of 3,3-diphenyl-propylbromide in 10 ml ethanol. The solution is stirred 24 hours at room temperature and evaporated under vacuum. The residue, dissolved in methylene chloride, is washed twice with an aqueous solution of sodium hydroxide at 5% and twice with water.

The solution is dried and evaporated under vacuum. The residual oil is dissolved in ethanol saturated with hydrogen chloride and evaporate under vacuum. The product is recrystallized from ethylacetate. 1.6 g N-(methyl)-3,3-diphenylpropylamine hydrochloride having m.p. 177°–178° C. are obtained.

To a solution of 3.37 g (0.015 moles) of N-(methyl)-3,3-diphenylpropylamine and 4.5 ml triethylamine in 40 ml toluene kept under reflux, is added, under stirring, a solution of 3.465 g (0.015 moles) of 3-phenylthiopropylbromide in 10 ml toluene. The mixture is stirred and refluxed for 15 hours. After cooling the precipitated triethylamine bromide is filtered off and the solution is washed three times with water, dried and the solvent evaporated. The residue is dissolved in a mixture chloroform/methanol 97/3 and purified by chromatography in a silica-gel column. The eluted fraction corresponding to the desired product, is evaporated, dissolved in ethanol saturated with hydrogen chloride, evaporated and the residual oil is treated with ethyl ether. Obtained 2.1 g of a product having m.p. 113°–114° C. Rf=0.35.

EXAMPLE 7

Preparation of
N-(3'-p-hydroxyphenylthiopropyl)-3-(p-hydroxyphenyl)-3-(phenyl)propylamine hydrochloride To a stirred and refluxing solution of 3.39 g (0.0122 moles) of 3-(p-methoxy)-3-(phenyl)propylamine in 30 ml toluene containing 4 ml triethylamine is gradually added a solution of 3.18 g (0.0122 moles) of 3-(p-methoxyphenylthiopropylbromide in 20 ml toluene. After refluxing for 15 hours the solution is cooled, filtered, washed twice with water, dried and evaporated under vacuum. The residue, dissolved in 30 ml chloroform and the solution washed twice with hydrochloric acid 6 N, three times with warm water, dried and evaporated under vacuum.

The product crystallizes slowly from n-propanol/ethyl ether 1/5. Obtained 2.4 g, m.p. 107°–109° C.

1.95 g (0.0041 moles) of the product obtained above are dissolved in 30 ml methylene chloride and cooled to $-60°--70°$ C. A cooled solution of 2.11 ml of boron tribromide in 15 ml methylene chloride is gradually added. The mixture is kept 1 hour at low temperature and 24 hours at room temperature. While cooling with brine, water, (45 ml) is gradually added. The aqueous layer is neutralized with sodium hydroxide 1 N. The organic layer separated, washed with water, dried and evaporated. The obtained oil is dissolved in ethanol saturated with hydrogen chloride. After evaporation of the solvent under vacuum the residue is crystallized from ethanol/ethylacetate 1/9.

Obtained 1.1 g of the desired product having m.p. 159°–161° C.

I claim:
1. N-(3'-p-hydroxyphenylthiopropyl)-3,3-diphenylpropylamine and its pharmaceutically acceptable salts.

* * * * *